United States Patent [19]

Khosravi

[11] Patent Number: 5,415,637
[45] Date of Patent: May 16, 1995

[54] TEMPORARY STENTING CATHETER WITH DRUG DELIVERY CAPABILITIES

[75] Inventor: Fahrad Khosravi, Belmont, Calif.

[73] Assignee: Advanced Cardiovascular Systems, Inc., Santa Clara, Calif.

[21] Appl. No.: 47,270

[22] Filed: Apr. 14, 1993

[51] Int. Cl.⁶ .................................. A61M 29/00
[52] U.S. Cl. ................................ 604/105; 604/53; 606/198
[58] Field of Search .................. 604/104–109, 604/49–55; 606/191, 192, 194, 196, 198

[56] References Cited

U.S. PATENT DOCUMENTS

| | | | |
|---|---|---|---|
| 102,985 | 5/1870 | Snyder | 604/104 |
| 295,276 | 3/1884 | Palmer | 604/104 |
| 837,085 | 11/1906 | Loar | 604/108 |
| 4,323,071 | 4/1982 | Simpson et al. | 128/343 |
| B1 4,323,071 | 5/1990 | Simpson et al. | 128/343 |
| 4,332,254 | 6/1982 | Lundquist | 128/344 |
| 4,439,185 | 3/1984 | Lundquist | 604/97 |
| 4,468,224 | 8/1984 | Enzmann et al. | 604/247 |
| 4,516,972 | 5/1985 | Samson | 604/282 |
| 4,538,662 | 9/1985 | Samson et al. | 128/772 |
| 4,582,181 | 4/1986 | Samson | 128/348.1 |
| 4,583,969 | 4/1986 | Mortensen | 604/49 |
| 4,585,000 | 4/1986 | Hershenson | 604/108 X |
| 4,597,755 | 7/1986 | Samson et al. | 604/96 |
| 4,616,652 | 10/1986 | Simpson | 128/344 |
| 4,748,982 | 6/1988 | Horzewski et al. | 128/344 |
| 4,771,778 | 9/1988 | Mar | 128/344 |
| 4,790,315 | 12/1988 | Mueller, Jr. et al. | 128/344 |
| 4,793,350 | 12/1988 | Mar et al. | 128/344 |
| 4,850,958 | 7/1989 | Berry et al. | 604/53 X |
| 4,911,689 | 3/1990 | Hattler | 604/49 X |
| 4,921,484 | 5/1990 | Hillstead | 604/104 |
| 4,994,033 | 2/1991 | Shockey et al. | 604/101 |
| 4,998,539 | 3/1991 | Delsanti | 128/898 |
| 5,002,560 | 3/1991 | Machold et al. | 606/198 |
| 5,034,001 | 7/1991 | Garrison et al. | 604/53 |
| 5,037,383 | 8/1991 | Vaslef et al. | 604/49 X |
| 5,049,132 | 9/1991 | Shaffer et al. | 606/194 X |
| 5,087,244 | 2/1992 | Wolinsky et al. | 604/53 |
| 5,098,376 | 3/1992 | Berry et al. | 604/49 X |
| 5,133,732 | 7/1992 | Wiktor | 606/195 |
| 5,180,368 | 1/1993 | Garrison | 604/104 |
| 5,193,533 | 3/1993 | Body et al. | 604/105 X |
| 5,213,576 | 5/1993 | Abiuso et al. | 606/192 X |

FOREIGN PATENT DOCUMENTS 2651440 3/1991 France .................. 604/53

*Primary Examiner*—John D. Yasko
*Assistant Examiner*—Frank Wilkens
*Attorney, Agent, or Firm*—Fulwider, Patton, Lee & Utecht

[57] ABSTRACT

An intravascular catheter having an expandable region formed of hypotubes mounted on the distal end of a tubular member that is capable of delivering a drug to the artery and radial expansion and contraction by means of a control wire. Each of the hypotubes has at least one surface aperture and the lumen of each of the hypotubes is in fluid communication with a drug delivery lumen. A therapeutic drug is injected into the patient's vasculature through the apertures in the hypotubes. The catheter is particularly adapted to hold open an artery after a vascular procedure therein such as a balloon angioplasty or other types of vascular procedures, and if desired to introduce a drug to the site of the vascular procedure.

13 Claims, 2 Drawing Sheets

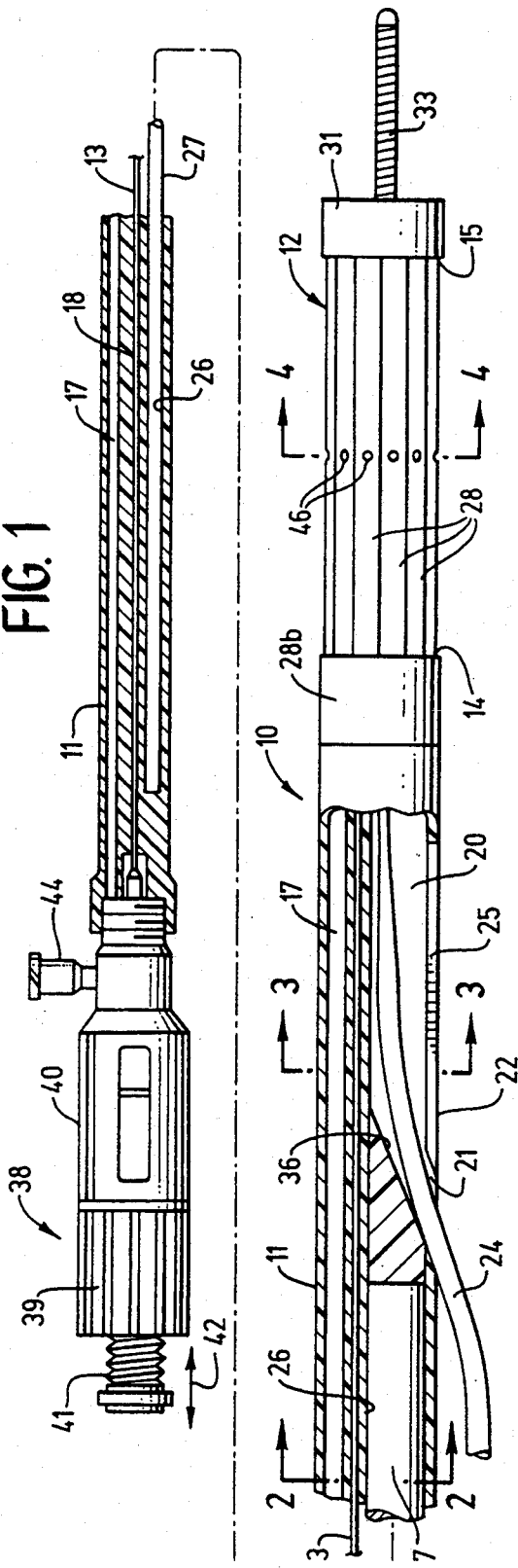
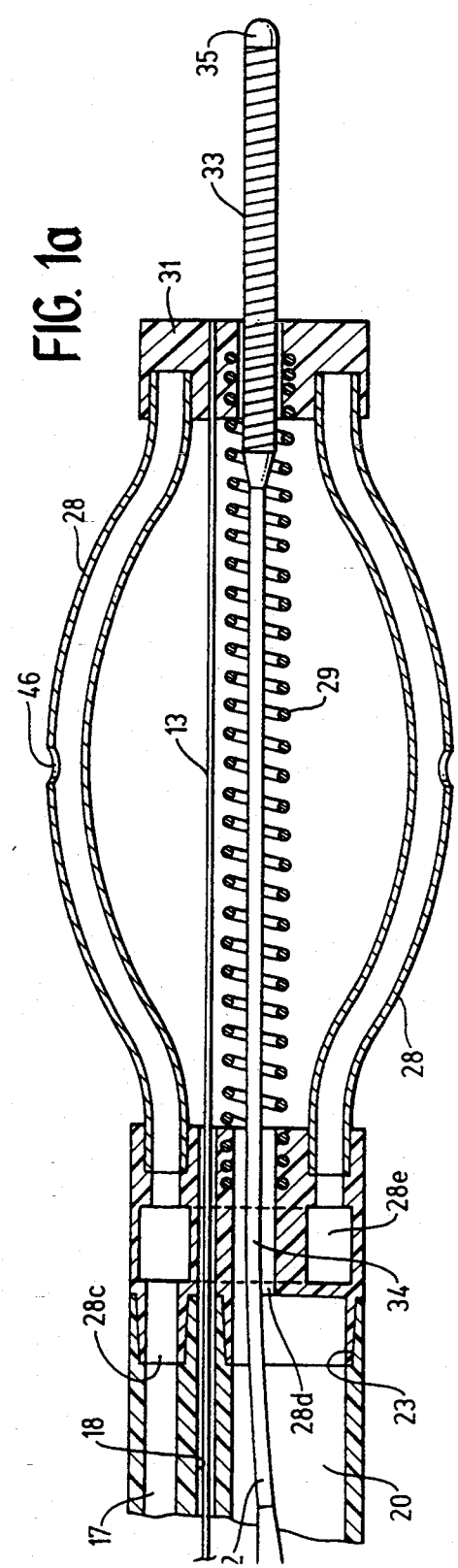

TEMPORARY STENTING CATHETER WITH DRUG DELIVERY CAPABILITIES

BACKGROUND OF THE INVENTION

This invention generally relates to vascular catheters suitable for maintaining the patency of a blood vessel after a vascular procedure therein, such as angioplasty.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guidewire and a dilatation catheter having an inflatable balloon on the distal end thereof are introduced through the guiding catheter with the guidewire slidably disposed within an inner lumen of the dilatation catheter. The guidewire is first advanced out of the distal end of the guiding catheter and is maneuvered into the patient's coronary vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., greater than about 4 atmospheres) and is inflated to a predetermined size (preferably the same as the inner diameter of the artery at that location) to radially compress the atherosclerotic plaque of the lesion against the inside of the artery wall to thereby dilate the lumen of the artery. The balloon is then deflated so that the dilatation catheter can be removed and blood flow resumed through the dilated artery.

By way of example, further details of angioplasty procedures and the devices used in such procedures can be found in U.S. Pat. No. 4,323,071 (Simpson-Robert), U.S. Pat. No. 4,332,254 (Lindquist), U.S. Pat. No. 4,439,185 (Lundquist), U.S. Pat. No. 4,168,224 (Enzmann, et al.), U.S. Pat. No. 4,516,972 (Samson), U.S. Pat. No. 4,582,181 (Samson), U.S. Pat. No. 4,538,622 (Samson, et al.), U.S. Pat. No. 4,597,755 (Samson), U.S. Pat. No. 4,616,652 (Simpson), U.S. Pat. No. 4,748,982 (Horzewski, et al.), U.S. Pat. No. 4,771,778 (Mar), and U.S. Pat. No. 4,793,350 (Mar, et al.) which are hereby incorporated herein in their entirety.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon the deflation of the balloon, a section of the dissected lining (commonly termed "flap") will collapse into the bloodstream, thereby closing or significantly reducing the blood flow through the vessel. In these instances, emergency bypass surgery is usually required to avoid a myocardial infarct distal to the blockage.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In recent years, various devices and methods (other than bypass surgery) for prevention of restenosis and repairing damaged blood vessels have become known which typically use an expandable cage or region (commonly termed "stent") on the distal end of the catheter designed to hold a detached lining against an arterial wall for extended periods to facilitate the reattachment thereof. Some stents are designed for permanent implantation inside the blood vessel and others are designed for temporary use inside the vessel. By way of example, several stent devices and methods can be found in U.S. Pat. No. 4,998,539, U.S. Pat. No. 5,002,560, U.S. Pat. No. 5,034,001 (Garrison, et al.), U.S. Pat. No. 5,133,732 (Wiktor), and U.S. Pat. No. 5,180,368 (Garrison).

Typically, the expandable region of these stents is formed by a braided wire attached to the distal end of the catheter body. Such braided designs are difficult and expensive to manufacture, and create reliability concerns due to the existence of high stress points located at the connection of the braided wire region with the catheter body and at the connections between the intermingled wire strands.

Alternatively, or in addition to the use of stents, various drugs may be applied to the site of the dilated lesion to prevent or reduce chances of restenosis and to aid in the healing of flaps, dissection or other hemorrhagic conditions that may appear after an angioplasty procedure. However, the braided wire stents are not designed for delivering or injecting drugs to the specific site of the lesion while adequate flow is maintained in the vascular lumen.

What has been needed and heretofore unavailable is an easily advanceable and removable low-profile intravascular catheter which can hold a collapsed dissected lining or flap against the blood vessel wall for sufficient time to allow the natural adhesion of the flap to the blood vessel wall and which can allow the simultaneous delivery or injection of a drug to the collapsed dissected lining to aid in the adhesion process and to aid in the prevention of restenosis while simultaneously allowing for the perfusion of blood to locations distal to the catheter without blocking a branch artery. The present invention fulfills this need.

SUMMARY OF THE INVENTION

This invention is directed to a vascular catheter which can hold a blood vessel open for a long period of time after a vascular procedure therein and which allows for the perfusion of blood through the blood vessel while the blood vessel is held open and which also allows for the delivery or the injection of drugs intraluminally and endoluminally after the dilatation procedure therein.

The vascular catheter in accordance with the present invention includes an elongated catheter body formed by a tubular member having a first inner lumen which extends through essentially the entire length of the body and a second, much shorter lumen in the distal portion of the catheter body which is adapted to receive a guiding member therein and which extends through the distal portion from a proximal opening in the sidewall of the distal portion to an opening in the distal end of the catheter body.

An expandable region is formed by a plurality of hypotubes positioned around the perimeter of the catheter body. The proximal ends of the hypotubes are secured at the proximal joint which is affixed to the catheter body. The distal end of the hypotubes are secured at the distal joint or collar and not to the catheter body. Thus, relative to the catheter body, the proximal joint is fixed and the distal joint is free to move longitudinally. An opening is provided in the distal collar connecting the distal end of the hypotubes so that a guiding member may pass therethrough.

A control wire extends through the first inner lumen of the tubular member and the interior of the expandable region with the distal end thereof connected to the distal joint which connects the distal end of the hypotubes. A flexible tubular guide, such as a coiled spring or a flexible tubular member, is provided on the interior of the expandable region between the ends thereof to ensure the proper passage of the guidewire therethrough. If not properly guided, the guidewire can diverge out of its travel path and move towards the inside of the expandable region. Longitudinal movement of the control wire forces the distal collar and the distal end of the hypotubes that are connected to the distal collar to move accordingly. Such movement adjusts the axial spacing between the proximal and distal end of the hypotubes which thereby allows the hypotubes to function as an expandable region which can deform to a larger diameter when the control wire is moved proximally and extend to the original diameter when the control wire is extended distally. When the expandable region is in the expanded position, the adjacent hypotubes are not completely in contact with one another and an opening is created between each pair of adjacent hypotubes. Preferably, the control wire is sufficiently stiff so that movement thereof in the distal direction will cause the expandable region to elongate without bending or kinking the wire. This eliminates the need for biasing the expandable region in some manner to return to an elongated state with minimal radial dimensions after the expansion thereof to allow for the ready removal of the catheter from the blood vessel. A suitable manipulator is provided on the proximal end of the catheter assembly to longitudinally move the control wire within the first lumen of the tubular member.

The relatively short, second inner lumen disposed within the distal portion of the tubular member is preferably defined in part by a sidewall in the distal portion of the tubular member which is provided with an elongated slot extending distally from the proximal hole in the sidewall to a location proximally adjacent the proximal end of the expandable region. This slotted construction greatly facilitates the rapid exchange of the vascular device of the invention over an in-place guidewire.

The proximal opening or port of the second inner lumen should be spaced proximally more than about 15 cm but less than about 60 cm, preferably from about 20 cm to about 50 cm, from the distal end of the catheter to ensure that the proximal opening in the sidewall of the tubular body does not extend beyond the distal end of the guiding catheter during a vascular procedure because the guidewire tends to form a loop if not restrained in some manner when the vascular catheter of the invention is pulled proximally. Loop formation can interfere with the subsequent removal of the catheter device through the guiding catheter.

The proximal end of the catheter is provided with an injection/delivery port for introduction of a drug or other desired fluids via the first inner lumen of the catheter to the lumen of the hypotubes. The drug delivery capability of the present invention is achieved by having one or more holes in the distal region of the hypotubes, whereupon reaching a sufficiently high pressure, the drug or fluid in the hypotubes exits through the holes and moves into the vascular site adjacent to the holes.

In a presently preferred embodiment, the proximal portion of the tubular body is provided with a third inner lumen which has disposed therein a stiffening member or stylet which adds to the pushability of the catheter and facilitates the advancement thereof through a patient's vascular system.

The vascular catheter of the invention allows for the rapid advancement thereof over a guidewire or other guiding member to a vascular location wherein an occlusion has occurred. The expandable region when expanded will hold the blood vessel open and simultaneously allow blood flow through the expandable region thereby eliminating or preventing ischemic conditions distal to the occlusion. Importantly, the vascular catheter of the invention is capable of delivering drugs or other fluids of interest to the site of the occlusion for treatment of the vascular site. In addition, the vascular catheter of the present invention can be mounted and withdrawn from an in-place guidewire without the use of extension wires and the like which can greatly increase the overall time for the procedure. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in cross-section, of an intravascular catheter embodying features of the invention;

FIG. 1a is an elevational view of the expandable region of the catheter shown in FIG. 1 in the expanded condition;

DETAILED DESCRIPTION OF THE INVENTION

Figure 2:
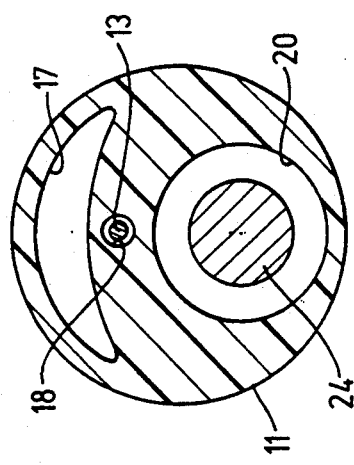
FIG. 2 is a transverse cross-sectional view of the catheter shown in FIG. 1 taken along lines 2—2.
Figure 3:
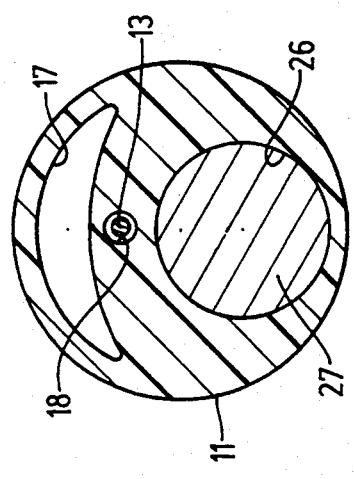
FIG. 3 is a transverse cross-sectional view depicting the catheter shown in FIG. 1 taken along lines 3—3.
Figure 4:
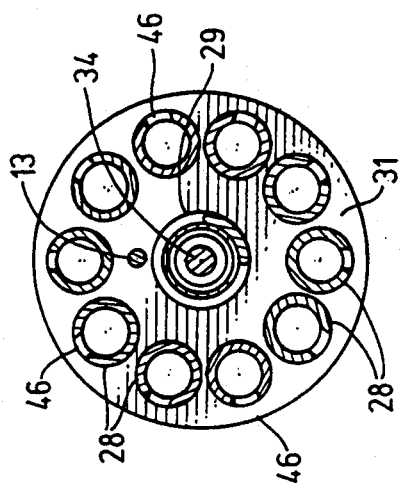
FIG. 4 is a transverse cross-sectional view of the catheter shown in FIG. 1 taken along lines 4—4.

FIGS. 1–4 illustrate an intravascular catheter assembly 10 embodying features of the invention. Catheter assembly 10 generally includes an elongated catheter body 11, an expandable region 12 secured to the distal end of the catheter body and a control wire or cable 13 for adjustment of the axial distance between the proximal end 14 and the distal end 15 of the expandable region 12 to vary the radial expansion thereof.

The elongated tubular member which forms catheter body 11 has a first inner lumen 17 and a second inner lumen 18 which extend through essentially the entire length thereof. Second inner lumen 18 is adapted to receive control wire 13. A third much shorter inner lumen 20 is provided in the distal portion of catheter body 11. Third inner lumen 20 extends from side port 21 in sidewall 22 of tubular catheter body 11 to port 23 provided in the distal end of the catheter body. A guiding member 24 is slidably disposed within the relatively short inner lumen 20 to facilitate the rapid advancement and replacement of catheter assembly 10. A longitudinal slit 25 is preferably provided in sidewall 22 which extends distally from side port 21. A fourth inner lumen 26 may be provided within catheter body 11 which extends from a location proximal to side port 21 to essentially the proximal end of the tubular member. A rod or stylet 27 fits within fourth inner lumen 26 to provide additional stiffness to catheter assembly 10 proximal to side port 21 to increase its pushability.

Expandable region 12 is formed from a plurality of hypotubes 28, each having a lumen, arranged alongside one another in a substantially cylindrical fashion. The number of hypotubes 28 forming expandable region 12 typically varies from about 4 to about 16, preferably from about 6 to about 12. The diameter of hypotubes 28 for coronary vasculature applications typically vary from about 0.011 to about 0.015 inches, preferably about 0.013 inches. For applications other than coronary vasculature, the diameter of the hypotubes can be modified accordingly. The arrangement of the hypotubes as described above is simply one of various possible arrangements which can allow the expandable region to radially expand and contract as desired. For example, the hypotubes can be woven together in a braided fashion or they can be arranged in a spiral fashion. A flexible tubular element 29 is provided within the interior of expandable region 12 between proximal and distal ends 14 and 15 thereof to guide guiding member 24 through the interior of the expandable region. Proximal ends 14 of hypotubes 28 forming the expandable region are bonded at proximal joint 28b to the catheter body by suitable means such as use of an adhesive. Proximal joint 28b can be formed of a manifold that is bonded to the catheter body and has a first opening 28c on its proximal side to first inner lumen 17 and a second opening 28d for the passage of guiding member 24 therethrough. The proximal joint has a chamber 28e which allows fluid communication between first opening 28c and the lumen of hypotubes 28 beginning at proximal ends 14. Chamber 28e is closed to second opening 28d. Distal ends 15 of hypotubes 28 are bonded together by suitable means such as an adhesive to form distal collar 31. Distal collar 31 has a central passageway for the guiding member to advance therethrough. The distal end of control wire 13 is also fixed to distal collar 31 which is slidably mounted about flexible tubular element 29 so that longitudinal or axial movement thereof adjusts the axial spacing between proximal and distal ends 14 and 15 of the expandable region, thereby varying the radial dimension thereof. Hypotubes 28 of expandable region 12 should have sufficient strength and be used in sufficient numbers so that the expandable region is capable of supporting an external pressure of at least 4 psi to ensure that a flap can be properly held in position within a patient's artery.

Guidewire 24 comprises a core member 32, a helical coil 33 or other flexible body disposed about and fixed to tapered distal portion 34 of the core member. A rounded plug 35, preferably formed of radiopaque material, is provided at the distal tip of coil 33. The construction of the distal portion of guidewire 24 can have a conventional structure with core member 32 extending through helical coil 33 to plug 35, or with the core member terminating short of plug 35 and a shaping ribbon (not shown) extending from core member 32 to plug 35. Guide member 24 extends through third inner lumen 20 disposed within the distal portion of the tubular member and out of distal port 23, through flexible tubular guiding element 29 which extends through the interior of expandable region 12 and out the distal end thereof through distal collar 31. An incline or ramp 36 is provided at the proximal end of third inner lumen 20 at the entryway of side port 21 to facilitate the insertion and withdrawal of guidewire 24 therethrough.

The distance between distal end 15 of expandable region 12 and side port 21 should be at least 15 cm but not greater than 60 cm, preferably from about 20 to about 50 cm, so that when the expandable region is expanded within a patient's vascular system to hold a blood vessel open, side port 21 of catheter assembly 10 will remain within the interior of a guiding catheter to ensure that guiding member 24 does not have the opportunity to form a loop when the catheter assembly is pulled back into the guiding catheter.

A manipulator adapter 38 is provided on the proximal end of catheter body 11 to effect longitudinal movement of the control wire 13. Internally threaded cap 39 is secured to the proximal end of manipulator housing 40. Axial rotation of cap 39 causes the longitudinal movement of internal member 41 as shown by arrow 42, and as a result controls the axial spacing between proximal and distal ends 14 and 15 of expandable region 12 and thus the radial dimension thereof. If control wire 13 is relatively stiff, it can be employed to extend ends 14 and 15 of expandable region 12 away from one another, elongating the expandable region so that it can be removed from a blockage. If not, control wire 13 can be used to shorten the spacing between ends 14 and 15, but hypotubes 28 of the expandable region can be formed in a biased condition so that upon release of the manipulator, the expandable region returns to its elongated condition. An indicator 43 is provided on internal member 41 to display the radial dimension of expandable region 12.

Other means can be employed to return expanded region 12 to an elongated condition. For example, as previously mentioned, a spring may be provided between ends 14 and 15 and be biased to cause the same elongation. Additionally, the hypotubes can be formed of a metal such as nitinol which has a "memory" to allow expandable region 12 to change shape with changes in temperature. An electrical current can be passed through the hypotubes to resistively heat the tubes and thereby change the shape thereof, or a hot or cold fluid could be introduced in the hypotubes to trigger a mechanical response resulting in a change in the shape. The hypotubes could also be formed with a memory to either expand or contract in response to a temperature variance. In such a case, the control wire could be used to return the hypotubes to the desired shape. It is also possible to set the shape memory temperature of the hypotubes well below that of the blood to give the hypotubes pseudo-elastic properties. In such a case, pulling control wire 13 will cause hypotubes 28 to expand and releasing the control wire will cause the hypotubes to collapse or extend to their original position.

Manipulator 38 has a side arm 44 to inject therapeutic drugs or other desired fluids such as heparinized saline through first inner lumen 17. Solutions such as heparinized saline can be used to keep the lumen free of blood and to prevent the formation of thrombi in the inner lumen or in the expandable region. Further details of the manipulator can be found in U.S. Pat. No. 5,002,560 entitled EXPANDABLE CAGE CATHETER WITH A ROTATABLE GUIDE.

To use the drug delivery capability of the catheter of the invention, a drug is injected into the first inner lumen that may be in the form of an already mixed solution or it may be in the form of pellets that could be carried through the lumen by a proper fluid transport medium. The drug or other fluid injected into first inner lumen 17 travels distally and enters proximal joint 28b which acts as a manifold via first opening 28c in the proximal joint and moves into chamber 28e to subsequently flow into hypotubes 28. Once inside the hypotubes, the drug or other fluid of interest continues to travel distally and exits through one or more holes 46 that have been previously placed in the hypotubes 28. Some holes may be placed in each hypotube at its most radially outward surface and some holes may be placed at other surface locations of each hypotube. The holes must be large enough to allow passage of fluid or properly sized pellets mixed in the fluid. Upon exiting through holes 46 in the distal region of the hypotubes, the drug or other fluid of interest enters the patient's artery. When expandable region 12 is in the expanded position, the holes that are placed on the most radially outward surface of the hypotubes are in contact with the endoluminal layer of the artery, and with a sufficiently high pressure exerted by the expansion of the expandable region, the holes are embedded into the arterial wall. In such a position, with a sufficiently high enough infusion pressure, the drug or other fluid of interest may be injected into the tissue in chronic therapeutic applications (e.g., for treatment or prevention of restenosis). Alternatively, through the remaining holes in each hypotube or with a lower infusion pressure, the drug or fluid of interest could be released to the interior surface of the vascular lumen in case of acute and subacute therapy of flaps, dissection or other hemorrhagic indications. In the collapsed or extended position of the expandable region, the hypotube assembly could act as an infusion device, where a drug such as an anticoagulant or a thrombolytic fluid could be introduced inside the artery. It may be advantageous for the hypotubes forming the expandable region to have a radiopaque material disposed therein so that the position of the cage and of the holes in the hypotubes where the drug or fluid of interest enters the artery can be readily known.

Generally, the dimensions of the catheter assembly of the invention are essentially the same dimensions of vascular catheters used in angioplasty procedures. The overall length of the assembly may be about 100 to 175 cm. The diameter of the catheter body may range from about 0.035 to 0.06 inch. The expandable region in the unexpanded condition has approximately the same diameter as the catheter body but may be expanded to a maximum diameter of about 1 to about 10 mm. The diameter of first inner lumen 17 will depend upon the amount of fluid or drugs in the form of pellets which must pass therethrough. The diameter of second inner lumen 18 must be sufficiently large to allow control wire 13 to easily pass therethrough. The diameter of third inner lumen 20 should be sufficiently larger than the diameter of guiding member 24 to allow the catheter to be easily advanced and removed over the guiding member.

In the operation of catheter assembly 10 the distal end thereof is mounted onto the proximal end of a guiding member 24 such as a guidewire which has been positioned across the occluded portion of the arterial passageway. The proximal end of the guiding member is advanced proximally through the central passageway provided in distal collar 31, guided through the interior of expandable region 12 by flexible tubular guiding element 29 through port 23 leading into third inner lumen 20, through the third inner lumen, and then out of side port 21. The proximal portion of guiding member 24 extending out of side port 21 is then manually held while catheter assembly 10 is advanced over the guiding member through a previously positioned guiding catheter to a desired location within the patient's blood vessel, such as where a prior vascular procedure has been performed. Cap 39 on manipulator 38 is rotated to expand the expandable region and thereby to press a flap which may be obstructing the blood flow against the arterial wall and thereby maintain the patency of the artery. The expandable region is held in the expanded condition for sufficient time, typically about 15 minutes to 24 hours, to allow the dissected lining to heal with the flap being reattached to the artery wall. Treatment periods of up to three days or more are believed to be beneficial. During the period of expansion of the expandable cage, blood flows readily through the openings between the hypotubes forming the expandable region so that no ischemia occurs distal to the catheter either in the occluded artery or a side branch thereof.

After the detached flap has been resecured to the artery wall, expanded region 12 can be elongated by rotating the cap in a direction opposite to the direction for expanding the expandable region to reduce the radial dimensions thereof. Then catheter assembly 10 can be removed from the location within the patient's vasculature.

As the distal section of the catheter assembly emerges from the proximal end of the guiding catheter, guiding member 24 can be separated from the third inner lumen by pulling the guidewire through slit 25 which extends from side port 21 to a location adjacent the proximal end of hypotubes 28 of expandable region 12. This allows the guiding member to be manually held exterior to the guiding catheter while catheter assembly 10 of the invention is being exchanged for another catheter device.

Figure 5:
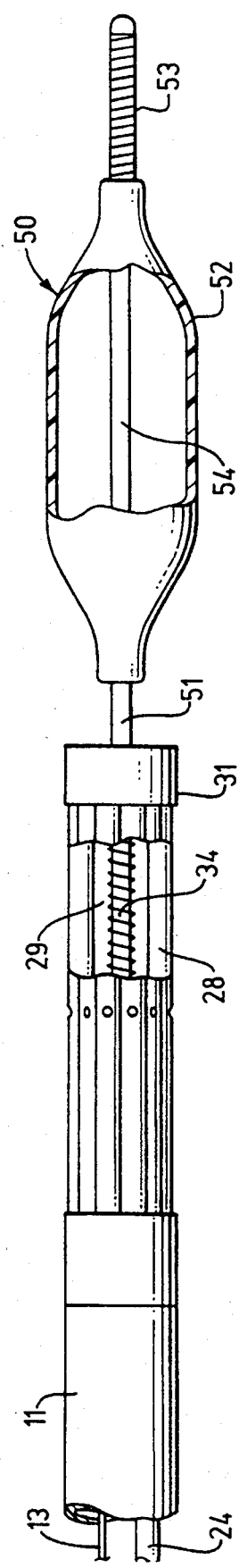
FIG. 5 is an elevational view of the intravascular device shown in FIG. 1, wherein the guiding member is a steerable low-profile dilatation catheter.

FIG. 5 illustrates an embodiment of the invention wherein guiding member 24 is a steerable low-profile dilatation catheter 50 which includes a tubular member 51, a dilatation balloon 52 and a helical coil 53 which is disposed about and secured to a core member 54. The proximal end of core member 54 may be secured to the interior of the distal portion of tubular member 51 or it may extend to the proximal end thereof. Further details of steerable dilatation catheters which are suitable for use as guiding members herein can be found in U.S. Pat. No. 4,582,350 (Samson), U.S. Pat. No. 4,771,778 (Mar), and U.S. Pat. No. 4,793,350 (Mar et al.), which have been previously incorporated herein, and U.S. Pat. No. 4,998,923 which is hereby incorporated herein in its entirety by reference. The operation and construction of these steerable dilatation catheters are adequately described in the aforesaid references and need not be repeated herein.

The catheter assembly of the invention is described herein to be employed after an angioplasty procedure to hold open an artery when a dissected portion of the arterial lining collapses and occludes the arterial lumen. In addition, the catheter assembly of the invention is capable of allowing a drug or other therapeutic solution to be delivered to the site of the vascular procedure (via the holes in the hypotubes) so that it may be either released into the general area of the lesion when the expandable region is in the collapsed position or it may be injected into the arterial wall when the expandable region is in the expanded position. Such a drug delivery capability may help in the repairing of a flap or the prevention of restenosis after an angioplasty procedure. Furthermore, the expandable region of the catheter of the invention may allow it to be used as a dilatation catheter. The assembly shown in FIG. 1 is particularly suitable for use with angioplasty catheters (not shown) having removable guiding members 24 such as disclosed in U.S. Pat. No. 4,323,071, previously referred to. The embodiment shown in FIG. 5 on the other hand includes a guiding member which is a low-profile steerable dilatation catheter. It will be recognized by those skilled in the art that the catheter of the invention can be used within a patient's vasculature system after vascular procedures other than angioplasty.

The catheter assembly of the invention may be formed of conventional materials of construction. For example, catheter body 11 can be made of suitable plastic materials such as polyethylene, polyvinylchloride, polyesters, polyimide polyfluoroethylene polymers and the like. The proximal portion may also be formed of a suitable metal such as stainless steel (i.e., hypotubing) to provide additional pushability to the catheter assembly. Control wire 13 and hypotubes 28 forming expandable region 12 may be formed of stainless steel but may be formed of other materials such as platinum-nickel alloys (e.g., 90 wt % Pt, 10 wt % Ni) or suitable plastics or even composites. A presently preferred alloy for the hypotubes is a platinum-rhodium-iridium alloy (e.g., 58 wt % Pt, 20 wt % Rh and 22 wt % Ir) which provides a higher level of strength with excellent radiopacity. Variations can be made in the composition to vary properties. Suitable ranges include 52-65 wt % Pt, 15-25 wt % Rh and 17-27 wt % Ir.

As can be appreciated, various modifications can be made to the present invention. For example, the catheter assembly of the invention may be provided with an inflatable dilatation balloon proximal or distal to the expandable region. In this manner, after dilatation of a stenosis by such a balloon, the position of the catheter assembly can be quickly shifted to position the expandable region thereof within the occlusion so that the hypotubes can be expanded to hold open the arterial passageway for sufficient time to tack up the flap against the arterial wall. The present invention also allows a drug to be introduced via the hypotubes to the site of the lesion to aid in the repairing of the flap or to aid in the prevention of restenosis. Other modifications can be made to the present invention without departing from the scope thereof.

What is claimed is:

1. An intravascular catheter for maintaining the patency of an arterial vasculature for an extended period and for delivering a therapeutic drug to the artery, the catheter comprising:

a) a catheter body having a first inner lumen, a second inner lumen, and a third inner lumen extending from a proximal guidewire port to a distal guidewire port which is adapted to receive a guidewire therein;

b) an expandable region formed of a plurality of hypotubes each having a lumen, a proximal end, a distal end and at least one surface aperture, said lumen of said hypotubes sealed at said distal end thereof and open at said proximal end thereof in fluid communication with said first inner lumen of said catheter body, said proximal end of said hypotubes attached to a distal end of said catheter body, said distal end of said hypotubes arranged with a passageway between said hypotubes for the passage of said guidewire therethrough;

c) a flexible tubular guide element extending through said expandable region and having an interior in communication with said third inner lumen of said catheter body and adapted to receive said guidewire therein;

d) a control wire disposed within said second inner lumen of said catheter body having a distal end attached to said distal end of said hypotubes and having means on a proximal end of said catheter body to move said control wire axially for adjusting the axial distance between said proximal and distal ends of said hypotubes thereby adjusting the radial dimension of said expandable region; and f) a port near said proximal end of said catheter body in fluid communication with said first inner lumen of said catheter body for introducing the therapeutic drug into said lumen of said hypotubes for delivery of the drug to the artery through said apertures in said hypotubes.

2. The intravascular catheter of claim 1 wherein, a manifold having a chamber in fluid communication with said first inner lumen of said catheter body and each of said lumen of said hypotubes connects said proximal end of said hypotubes to said distal end of said catheter body.

3. The intravascular catheter of claim 1 wherein, said third inner lumen is defined at least in part by a sidewall section of said catheter body with said proximal guidewire port extending through said sidewall section.

4. The intravascular catheter of claim 3 wherein, said sidewall section has a longitudinally extending slit therein which facilitates the rapid removal of said catheter from said guidewire.

5. The intravascular catheter of claim 4 wherein, said longitudinally extending slit extends distally from said proximal guidewire port to a location proximally adjacent said distal end of said third inner lumen.

6. The intravascular catheter of claim 1 wherein, said proximal guidewire port of said third inner lumen is positioned about 20 cm to about 50 cm from said distal end of said hypotubes forming said expandable region.

7. The intravascular catheter of claim 1 wherein, a fourth inner lumen is provided in said catheter body which extends from said proximal end of said catheter body to a location proximal to said proximal guidewire port of said third inner lumen.

8. The intravascular catheter of claim 7 wherein, said fourth inner lumen has a stiffening element disposed therein.

9. The intravascular catheter of claim 1 wherein, said expandable region is formed from about 4 to about 16 hypotubes.

10. The intravascular catheter of claim 1 wherein, said hypotubes are elongated tubes positioned alongside one another in a cylindrical arrangement.

11. The intravascular catheter of claim 1 wherein, said hypotubes forming said expandable region have a radiopaque material disposed therein.

12. An intravascular catheter for maintaining the patency of an arterial vasculature for an extended period and for delivering a therapeutic drug to the artery, the catheter comprising:
   a) an elongated catheter body having a proximal end, a distal end, a first inner lumen, a second inner lumen, and a third inner lumen extending therethrough;
   b) an expandable region defined by a plurality of hypotubes each having a lumen extending the length thereof and having a proximal end and a distal end, each said hypotube having at least one surface aperture, said proximal end of said expandable region connected to said distal end of said catheter body;
   c) means for adjusting the axial length of said hypotubes through said second inner lumen of said catheter body and thereby causing said hypotubes to expand radially outwardly; and
   d) a port near said proximal end of said catheter body in fluid communication with said first inner lumen for introducing the therapeutic drug into said lumen of said hypotubes for delivery of the drug to the artery through said apertures in said hypotubes.

13. A method for repairing an arterial vasculature having an occluded or partially occluded portion, comprising:
   a) providing a catheter having
      i) a catheter body having a first inner lumen, a second inner lumen, and a third inner lumen extending from a proximal guidewire port to a distal guidewire port which is adapted to receive a guidewire therein, said guidewire having a proximal end and a distal end;
      iii) an expandable region formed of a plurality of hypotubes each having a lumen, a proximal end, a distal end and at least one surface aperture, said lumen of said hypotubes closed at said distal end thereof and open at said proximal end thereof in fluid communication with said first inner lumen of said catheter body, said proximal end of said hypotubes attached to a distal end of said catheter body, said distal end of said hypotubes arranged to form a passageway between said hypotubes for the passage of said guidewire therethrough;
      iv) a flexible tubular guide element extending through said expandable region and having an interior in communication with said third inner lumen of said catheter body and adapted to receive said guidewire therein;
      v) a control wire disposed within said second inner lumen of said catheter body having a distal end attached to said distal end of said hypotubes and having control means on a proximal end of said catheter body to move said control wire axially so as to adjust the axial distance between said proximal and distal ends of said hypotubes forming said expandable region and thereby adjusting the radial dimension of said expandable region; and
      vi) a port near said proximal end of said catheter body in fluid communication with said first inner lumen of said catheter body for introducing a therapeutic drug into said lumen of said hypotubes for delivery of the drug to said artery via said apertures in said hypotubes;
   b) advancing said guidewire through said passageway provided between said hypotubes, through said flexible tubular guiding element within said expandable region, through said third inner lumen of said catheter body, and out said proximal guidewire port;
   c) positioning said distal end of said guidewire in the arterial vasculature across the site of the occlusion;
   d) advancing said catheter body over said guidewire until said expandable region is positioned across the site of the occlusion;
   e) manipulating said control means to move said control wire proximally thereby expanding said expandable region; and
   f) introducing the therapeutic drug through said apertures in said hypotubes so that said therapeutic drug is delivered to the site of the occlusion.

* * * * *